United States Patent [19]

Hayden et al.

[11] Patent Number: 5,407,513
[45] Date of Patent: Apr. 18, 1995

[54] APPARATUS AND PROCESS FOR CYCLICALLY ACCELERATING AND DECELERATING A STRIP OF MATERAL

[75] Inventors: Michael P. Hayden, Montgomery; Karl H. Stuermer, New Richmond, both of Ohio

[73] Assignee: The Procter & Gamble Company, Cincinnati, Ohio

[21] Appl. No.: 136,519

[22] Filed: Oct. 14, 1993

[51] Int. Cl.⁶ ............................................. B32B 31/00
[52] U.S. Cl. .................................... 156/265; 156/517; 156/519; 156/543; 156/552; 226/113; 226/114; 242/417
[58] Field of Search ................ 156/250, 265, 516, 517, 156/519, 543, 552, 361, 520, 521, 522; 226/113, 114; 242/75, 75.3

[56] References Cited

U.S. PATENT DOCUMENTS

| | | | |
|---|---|---|---|
| 3,897,293 | 7/1975 | Babcock | 156/265 X |
| 3,992,244 | 11/1976 | Craig et al. | 156/521 |
| 4,009,814 | 3/1977 | Singh | 226/113 |
| 4,798,353 | 1/1989 | Peugh | 226/114 X |
| 4,855,005 | 8/1989 | Jodrey | 156/361 |
| 4,863,086 | 9/1989 | Armelin | 226/114 X |
| 4,909,885 | 3/1990 | Swenson | 156/519 X |
| 4,925,520 | 5/1990 | Beaudoin et al. | 156/519 X |
| 5,045,134 | 9/1991 | Schenker et al. | 156/361 X |

*Primary Examiner*—David A. Simmons
*Assistant Examiner*—Paul M. Rivard
*Attorney, Agent, or Firm*—Jeffrey V. Bamber; Steven W. Miller; E. Kelly Linman

[57] ABSTRACT

The present invention discloses a method and apparatus for cyclically accelerating the leading end of a slower moving first material web to match the faster speed of a continuous second material web. The apparatus is comprised of a set of upstream metering rolls which feed the first material web at a constant slow speed, a set of downstream applicator rolls having a constant and relatively faster rotational velocity, and an acceleration mechanism which variably and alternately reverses and allows forward movement of a leading end segment of the first material web while allowing for the constant rotational velocities of the upstream and downstream rolls. The first material web is wrapped partially around the set of upstream rolls and the leading end segment thereof is wrapped partially around one of the downstream rolls. The acceleration mechanism is juxtapositioned between the upstream rolls and the downstream rolls in the feed path of the first material web. A cutting mechanism is provided for cutting a segment of predetermined length of the leading end segment of the first material web when the leading edge has been accelerated to match the speed of the downstream roll. The cut segment is thereafter applied by the applicator roll to the faster moving second material web. Thus, the present invention provides for matched speed cutting and matched speed application of a slower velocity first material onto a faster velocity second substrate material.

16 Claims, 6 Drawing Sheets

APPARATUS AND PROCESS FOR CYCLICALLY ACCELERATING AND DECELERATING A STRIP OF MATERIAL

BACKGROUND OF THE INVENTION

1. Technical Field

This invention relates generally to a method and apparatus for cyclically accelerating the leading end of a web material to match the faster speed of a downstream machine component. More specifically, a method and apparatus are disclosed for cutting and subsequently attaching strips of the web material onto a continuous faster moving substrate material.

2. Background Art

Modernly, disposable absorbent articles, such as diapers and catamenial pads, are manufactured utilizing a series of sequential and continuous high-speed operations. In one operation, relatively small fastener strips are cut from a leading end segment of a fastener material and subsequently secured to preselected portions of a continuous web of a substrate material. Traditionally, the substrate material is fed at a relatively high feed rate through a set of applicator rolls while a continuous length of the fastener material is fed at a low feed rate through a series of metering rolls. Moreover, the leading end of the fastener material is typically retained on, or in close proximity to one of the high speed applicator rolls. Thus, once the fastener strip is cut from the leading end of the fastener material, it is retained on the applicator roll for subsequent application to the preselected portion of the substrate material as it passes therethrough.

A problem inherent with such a continuous high speed manufacturing process involves the inability to precisely control the cut length and subsequent placement of the fastener strip due to the large difference in feed rates between the metering rolls and the applicator rolls. In one conventional method, the high velocity applicator roll is allowed to slip beneath the leading end of the fastener material. However, when a knife roll engages and cuts the fastener strip, the leading end of the fastener material is stretched beyond its normal length due to its momentary engagement with the faster underlying applicator roll. Unfortunately, there is a tendency for the remaining leading end of the fastener material to snap back and fall off of the applicator roll following the cutting operation.

Alternatively, it is known to intermittently reduce the velocity of the applicator roll and the knife roll until the fastener strip has been cut. Following the cutting operation, the applicator and knife rolls are rapidly accelerated to their normal rotational velocity. However, such rapid speed changes create undue stress and undesirable cyclical loading on the rolls and their respective drive systems. Moreover, such speed changes commonly result in excessive dimensional variations in the length of the fastener strip as well as inaccurate placement thereof on the substrate material.

Another system for cutting and applying the slow moving fastening material onto the faster moving substrate material uses the high speed applicator and knife rolls in combination with a set of high speed metering rolls. The fastener material is fed onto the applicator roll at high speed and then the metering rolls are rapidly reversed for extracting a predetermined length of the fastener material until the correct segment length is obtained and subsequently cut off. Unfortunately, this system also induces extreme stresses and cyclical loading within the metering rolls and their drive systems while still producing excessive dimensional variations in the final product. Thus, there is a need for an improved method and apparatus for intermittently cutting and applying a slow moving strip of material onto a continuous faster moving substrate material which is not burdened with the above-noted shortcomings.

SUMMARY OF THE INVENTION

In accordance with the present invention, a new and useful method and apparatus are disclosed for cyclically accelerating the leading end of a slower moving first material web. More specifically, the apparatus is comprised of a set of upstream metering rolls which feed the first material web at a constant slow speed, a set of downstream applicator rolls having a constant and relatively faster rotational velocity, and an acceleration mechanism which variably and alternately reverses and encourages forward movement of a leading end segment of the first material web while allowing for the constant rotational velocities of the upstream and downstream rolls. The first material web is wrapped partially around the set of upstream rolls and the leading end segment thereof is wrapped partially around one of the downstream rolls. Furthermore, the acceleration mechanism is juxtapositioned between the upstream rolls and the downstream rolls in the feed path of the first material web.

In the preferred embodiment, the acceleration mechanism is further defined as an eccentric accelerator having a carrier mounted for rotation on a driven shaft and a spindle eccentrically offset therefrom. The first material web is longitudinally fed around the upstream metering rolls and around a portion of the spindle on the eccentric accelerator such that its leading end segment is retained on one of the downstream rolls. The eccentric accelerator is operable for cyclically accelerating the leading end segment of the first material web to "match" the faster speed of the downstream rolls during the cutting operation. A further advantage of the present invention is that the rotational velocities of the upstream metering rolls and the downstream applicator rolls can be different and yet remain constant. This serves to eliminate the above-noted roll stresses, cyclical loading and process downtime encountered with traditional methods. Moreover, the eccentric accelerator can be easily installed into various process applications having a variety of roll speed differentials. Also, the machine components of the present invention are smaller in size, weight, and complexity as compared to the conventional systems. As a result, the products produced by this novel method and apparatus have superior dimensional accuracy.

Additional advantages and features of the present invention will become apparent from the following description and appended claims, taken in conjunction with the accompanying drawings.

BRIEF DESCRIPTION OF THE DRAWINGS

While the specification concludes with claims which particularly point out and distinctively claim the subject matter which is regarded as forming the present invention, it is believed that the invention will be better understood from the following description which is taken in conjunction with the accompanying drawings, in which:

DETAILED DESCRIPTION OF THE PREFERRED EMBODIMENT

Figure 1:
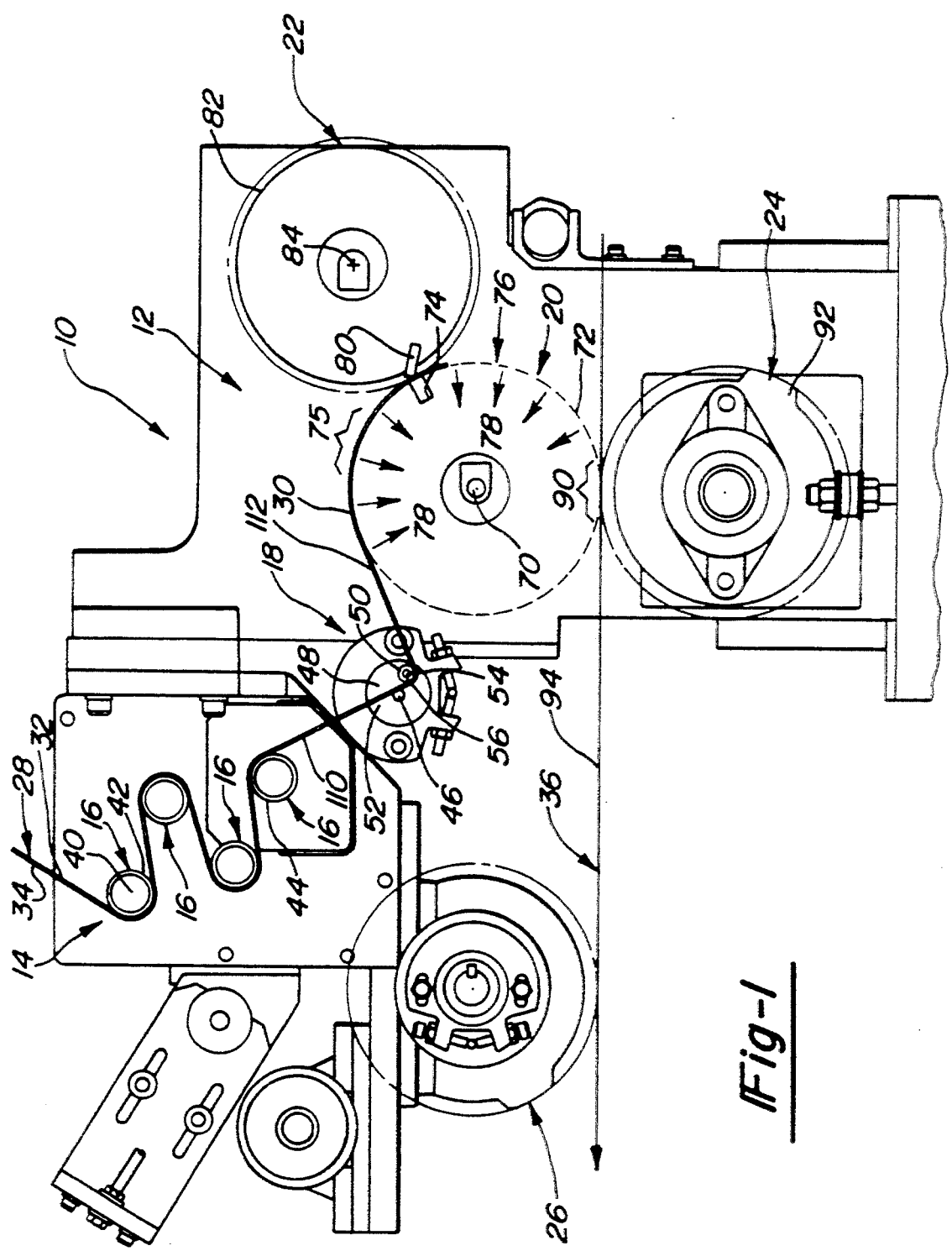
FIG. 1 is a side elevation view showing an eccentric accelerator in combination with an apparatus for cutting and applying a strip of fastener material onto a continuous substrate material.

The method and apparatus of the present invention are operable for cyclically accelerating and decelerating a strip of material and can be used within any manufacturing process having multiple speed rollers. In a preferred application, the method and apparatus of the present invention are used in combination with an automated machine 10 of the type used for applying a strip of a fastener material to a diaper substrate material. In general, machine 10 is comprised of a frame 12, a metering system 14 including a plurality of upstream metering rolls 16, an acceleration mechanism hereinafter referred to as eccentric accelerator 18, an applicator roll 20, a knife roll 22 and a pair of bump rolls 24 and 26. A web of fastener material 28 is continuously fed at a constant speed through upstream metering rolls 16 such that its leading end segment 30 is partially wrapped around a portion of applicator roll 20. In this particular instance, fastener material 28 is a film-like web with an adhesive coated side 32 and an opposing side 34 having a plurality of small discontinuous fastening projections extending outwardly therefrom. Fastener material 28 preferably has a high modulus of elasticity and a low mass. Simultaneously, a substrate diaper material 36 is being continuously fed at a constant speed between applicator roll 20 and bump roll 24.

Upstream metering rolls 16 each have a central drive shaft 40 surrounded by and connected to a cylindrically-shaped sleeve 42. Sleeve 42 has an outer arcuate surface 44 against which a portion of fastener material 28 is partially wrapped. Preferably outer arcuate surface 44 of each upstream metering roll 16 is treated, such as plasma coated, to prevent the build up of adhesive material from adhesive coated side 32 of fastener material 28. Furthermore, metering system 14 imparts a constant driving force on each drive shaft 40 such that outer arcuate surface 44 is driven at a constant rotational velocity denoted as $V_0$ (See FIG. 2).

Figure 2:
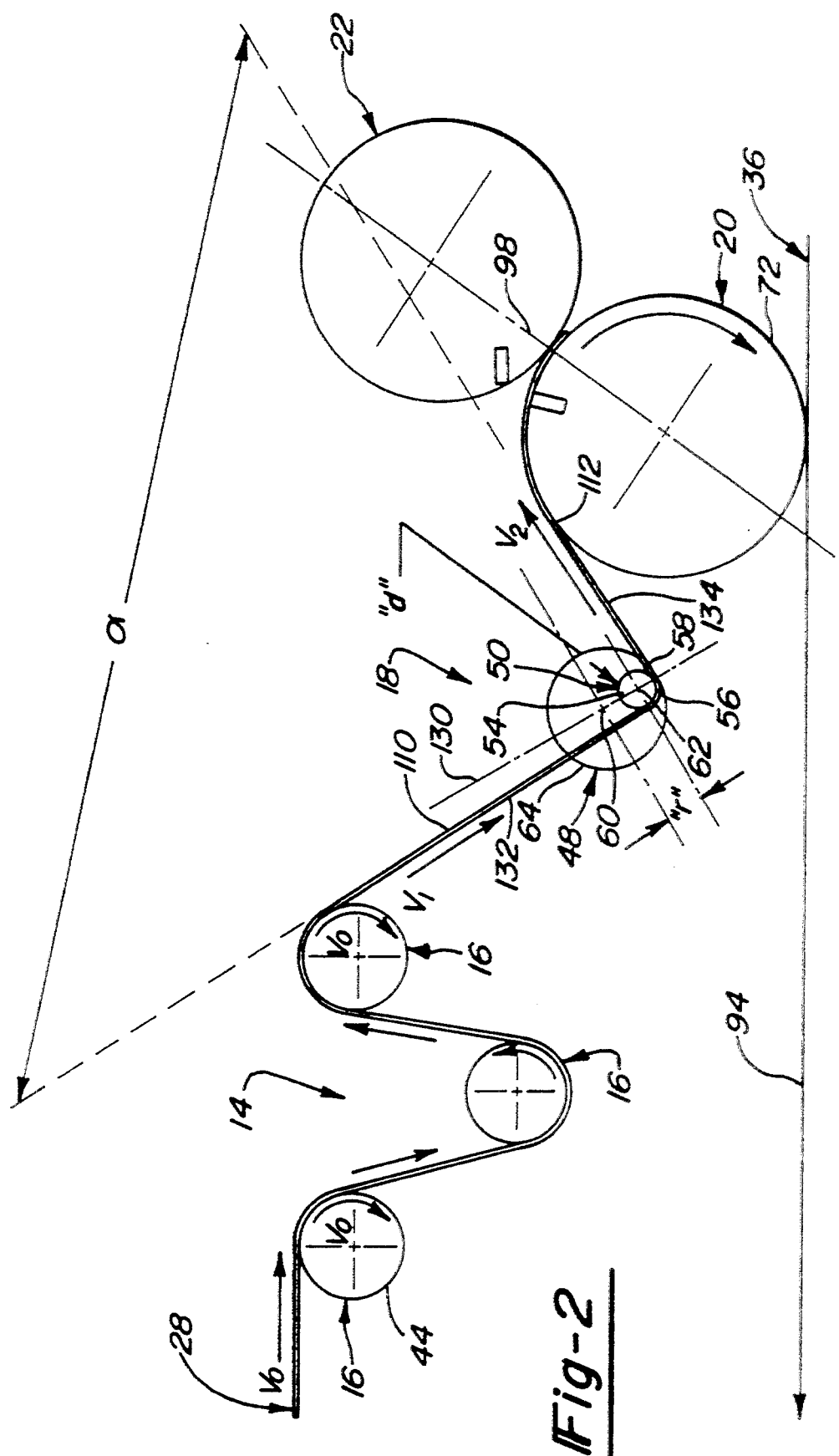
FIG. 2 is a diagrammatic representation of the eccentric accelerator and apparatus shown in FIG. 1.

Eccentric accelerator 18 is further comprised of a drive shaft 46, a carrier 48 and a spindle 50. Carrier 48 is disk-shaped and is mounted for rotation on drive shaft 46. Spindle 50 extends transversely from a face 52 of carrier 48 and is offset from drive shaft 46. Moreover, spindle 50 includes a central rod 54, a cylindrical sleeve 56 and a plurality of suitable bearings (not shown) located therebetween. As with upstream metering rolls 16, sleeve 56 has an outside surface 58 which is preferably plasma coated. In addition, spindle 50 is preferably made from a strong yet light weight material, such as aluminum, in order to minimize rotational inertia. As is best shown in FIG. 2, carrier 48 has a rotational axis 60 defined by the centerline of drive shaft 46. Similarly, spindle 50 also has a rotational axis 62 defined by the centerline of rod 54. The distance between the two offset rotational axes 60 and 62 is denoted as "r". Thus, upon driven rotation of carrier 48 about axis 60, spindle 50 is caused to rotate in a circular path 64 that is "r" distance away from axis 60. Moreover, outside surface 58 of sleeve 56 has a diameter denoted as "d".

With continued reference to FIG. 1, the downstream applicator roll 20 is shown supported and rotated by a central drive shaft 70. Applicator roll 20 further has an outer circumferential surface 72 with an anvil insert 74 radially extending inward from a portion thereof. In addition, a first portion 75 of outer circumferential surface 72 has leading end segment 30 of fastener material 28 engageably wrapped therearound. A semicircular portion of outer circumferential surface 72 also has a plurality of apertures 76 extending therethrough. A remote vacuum device (not shown) creates a negative pressure, as denoted by arrows 78, through a duct (not shown) and a stationary manifold (not shown) which, in turn, is connected to a ported rotating manifold (not shown) which is contained within roll 20. The rotating manifold is operably connected with apertures 76. This negative pressure acts to slidably retain leading end segment 30 of fastener material 28 to portion 75 of outer circumferential surface 72. However, the magnitude of the negative pressure must be sufficiently low such that eccentric accelerator 18 can variably decelerate, reverse and then allow the leading end segment 30 to accelerate and move in the direction of outer circumferential surface 72 of applicator roll 20. For example, a negative pressure that creates a frictional force of approximately 10 grams per linear inch is sufficient to retain fastener material 28 against applicator roll 20. Of course, one skilled in the art would know that the magnitude of the negative pressure used is dependent on the specific type of fastener material 28 and the required acceleration and deceleration rates, as well as the coefficient of friction of the material on the roll outer circumferential surface 72.

Knife roll 22 has a cutting device 80 or knife blade mounted on its cylindrically-shaped peripheral surface 82. Furthermore, knife roll 22 is rotatably driven by a central driving shaft 84. Moreover, the rotational velocity of knife roll 22 is matched with applicator roll 20. Therefore, cutting device 80 of knife roll 22 has a rotational velocity corresponding with that of applicator roll 20 such that cutting device 80 is rotationally matched with anvil insert 74. Therefore, cutting device 80 is adapted to cut off a cut segment 86 of fastener material 28. Cut segment 86 is retained against outer circumferential surface 72 of applicator roll 20 due to the negative pressure applied thereto.

With continued reference to FIGS. 1 and 2, the continuous web of substrate diaper material 36 is shown to be simultaneously fed between a second portion 90 of the applicator roll's outer circumferential surface 72 and a corresponding raised portion 92 of bump roll 24. Raised portion 92 of bump roll 24 has a rotational velocity equal to that of applicator roll 20. Furthermore, raised portion 92 is rotationally positioned to be proximate with second portion 90 of applicator roll 20 when cut segment 86 of fastener material 28 rotationally reaches second portion 90. Adhesive coated side 32 is then compressed against an upper surface 94 of diaper material 36. The outer circumferential surface 72 of applicator roll 20 and the manifolds are configured such that the negative pressure is not operable at this position proximate with bump roll 24. Referring to FIG. 2, diaper material 36 has a velocity equal to that of applicator roll 20 within ±0.5 percent. This provides for accurate positioning of cut segment 86 onto diaper material 36 and prevents deformation of these components during bonding.

In the preferred fastener and diaper application, eccentric accelerator 18 and applicator roll 20 have a rotational ratio of 3 to 1 which provides for eccentric accelerator 18 to be smaller and machine 10 to become more compact, however, such a rotational ratio can be any integer desired. In the example shown, the last upstream metering roll 16 is rotatably driven in a clockwise orientation as is applicator roll 20. However, carrier 48 of eccentric accelerator 18 is rotatably driven in a counterclockwise direction. Therefore, spindle 50 of eccentric accelerator 18 serves to alternately decelerate, reverse and then allow acceleration of leading end segment 30 of fastener material 24 as it follows circular path 64 upon rotation of carrier 48. Concurrently, upstream metering rolls 16 and applicator roll 20 maintain their respective constant direction and velocity. Substrate material 36 and fastener material 28 are both held under longitudinal tension to ensure accurate tracking on the rollers and to ensure a clean cut. In a preferred application, fastener material 28 is given a target speed of approximately four percent less than knife and applicator rolls, respectively 22 and 20, and substrate material 36 is given about a 0.625 percent strain.

Figure 3:
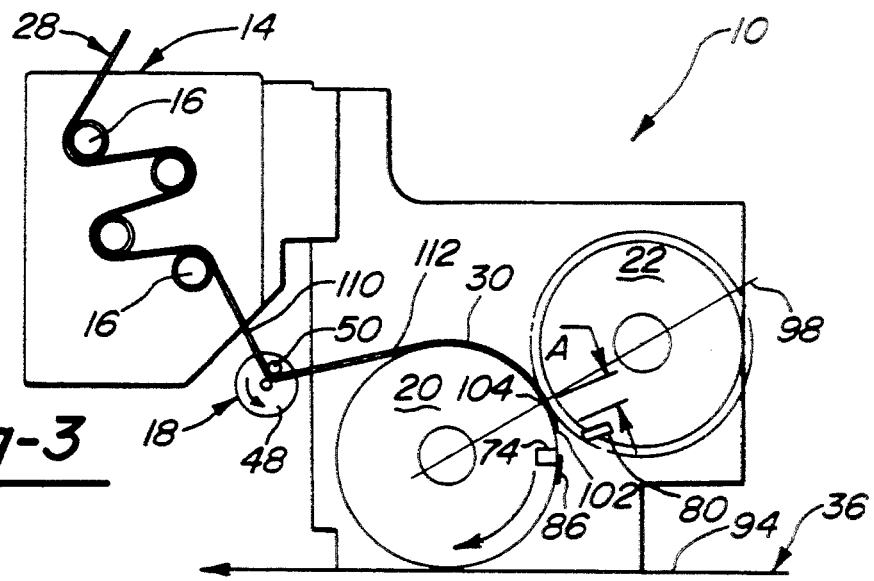
FIG. 3 is a side elevation view showing the eccentric accelerator in a first rotated position of its first cycle with an anvil roll and a knife roll in their respective first rotated positions.
Figure 4:
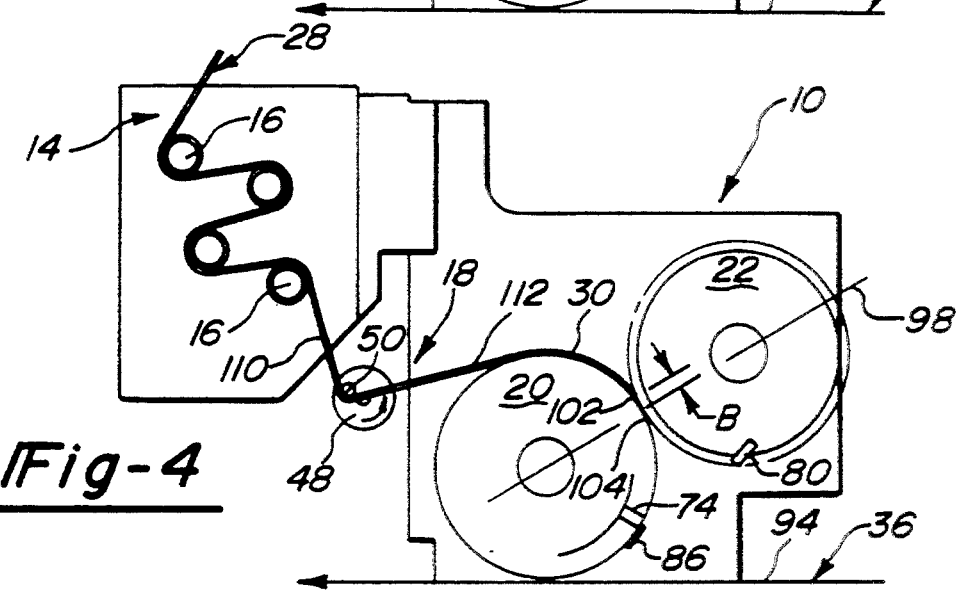
FIG. 4 is a side elevation view of the eccentric accelerator in a second rotated position of its first cycle with the anvil and knife rolls in their respective second rotated positions.

With particular reference now to FIGS. 3 through 13, a sequence of time elapsed positions for eccentric accelerator 18, applicator roll 20 and knife roll 22 is illustrated. The following sequence is directed to providing a cut segment 86 of fastener material 28 having a length 'L'. As such, exemplary intermittent lengths of leading end segment 30 relative to the line of contact 98 between applicator roll 20 and knife roll 22 are set forth to illustrate the sliding movement thereof during rotation of spindle 50 about circular path 64. Referring to FIG. 3, spindle 50 of eccentric accelerator 18 is shown in a first rotated position on circular path 64 in its first cycle with applicator roll 20 and knife roll 22 each shown in their respective first rotated positions. Accordingly, a predetermined length of fastener material 28 has a positive measurement denoted as 'A'. This measurement is taken between the distal edge 102 of leading end segment 30 of fastener material 28 and an intersection point 104 at line 98 between applicator roll 20 and knife roll 22. From FIG. 4, eccentric accelerator 18, applicator roll 20 and knife roller 22 are shown rotated to their respective time elapsed positions. Spindle 50 of eccentric accelerator 18 is shown in its second rotated position on circular path 64 in its first cycle which is diametrically opposed to applicator roll 20. Simultaneously, cutting device 80 and anvil insert 74 rotate with applicator roll 20 and knife roll 22 to their respective second rotated positions. During the counterclockwise rotation of carrier 48 between FIGS. 3 and 4, journalled sleeve 56 of spindle 50 is rotated counterclockwise on rod 54 about axis 62 and serves to reverse leading end segment 30. Accordingly, distal edge 102 of fastener material 28 is a negative distance 'B' away from point 104. In other words, as carrier 48 rotates, spindle 50 changes position which varies the path length of fastener material 28 between the last upstream metering roll 16 and applicator roll 20. Therefore, this path length rate of change (i.e., acceleration or deceleration) translates to the velocity of leading segment 30. Accordingly, the path length rate of change causes the clockwise or counterclockwise rotation of sleeve 56.

Figure 5:
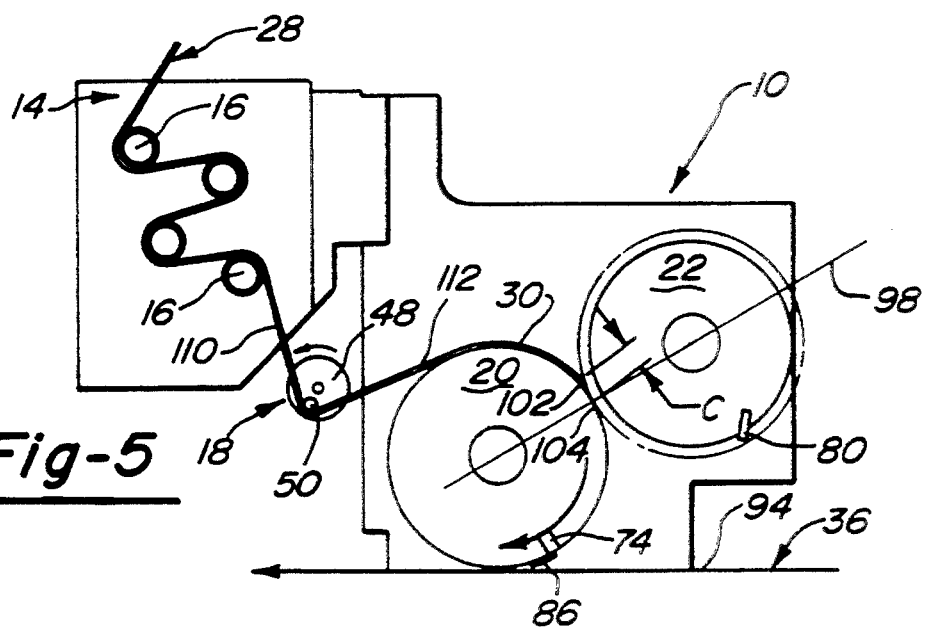
FIG. 5 is a side elevation view of the eccentric accelerator in a third rotated position of its first cycle with the anvil and knife rolls in their respective third rotated positions.

Referring to FIG. 5, eccentric accelerator 18, applicator roll 20 and knife roll 22 are shown rotated to their next respective time elapsed positions. Spindle 50 of eccentric accelerator 18 is shown in its third rotated position of its first cycle. Simultaneously, cutting device 80 and anvil insert 74 rotate with applicator roll 20 and knife roll 22 to their respective third rotated positions. During the counterclockwise rotation of carrier 48 about axis 60 between FIGS. 4 and 5, sleeve 56 of spindle 50 is caused to rotate counterclockwise about axis 62 and serves to continue the retraction of leading end segment 30. Therefore, distal edge 102 of fastener material 28 is a negative distance 'C' away from intersection point 104; 'C' is a greater negative distance than is 'B'.

Figure 6:
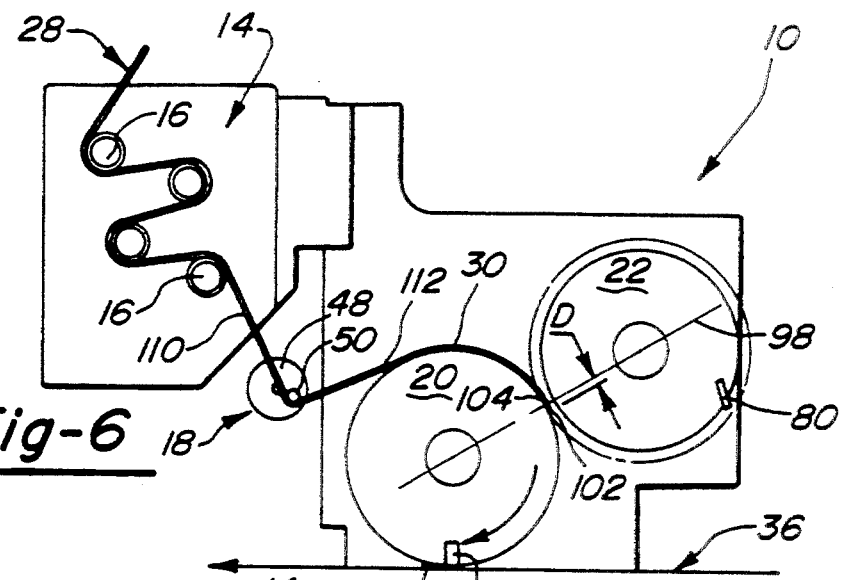
FIG. 6 is a side elevation view of the eccentric accelerator in a fourth rotated position of its first cycle with the anvil and knife rolls in their respective fourth rotated positions.

As is depicted in FIG. 6, eccentric accelerator 18, applicator roll 20 and knife roll 22 have now rotated to their next respective time elapsed positions. Spindle 50 of eccentric accelerator 18 is shown in its fourth rotated position along circular path 64 in its first cycle so as to be diametrically adjacent to applicator roll 20. Concurrently, cutting device 80 and anvil insert 74 rotate with applicator roll 20 and knife roll 22 to their respective fourth rotated positions. During the continued counterclockwise movement of carrier 48 between FIGS. 5 and 6, sleeve 56 of spindle 50 is rotated clockwise about axis 62 and allows leading end segment 30 to accelerate. Thus, distal edge 102 of fastener material 28 extends a positive distance 'D' beyond point 104 which is less than 'A'. Simultaneously, applicator roll 20 compresses cut segment 86 against substrate material 36 for attachment thereto. This is the "matched speed" position where leading end segment 30 has the greatest speed which is substantially equivalent to the rotational velocities of applicator and knife rolls 20 and 22, respectively. Referring to FIG. 2, at this position a pair of lines 130 and 132 are substantially parallel to one another and a line 134 is approximately ninety degrees ($\alpha$) from line 132.

Figure 7:
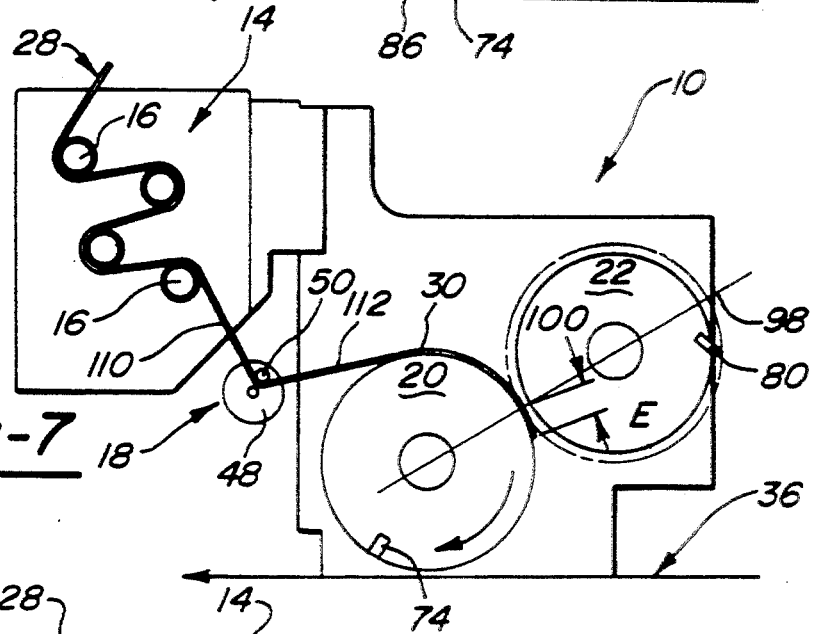
FIG. 7 is a side elevation view of the eccentric accelerator in a first rotated position of its second cycle with the anvil and knife rolls in their respective fifth rotated positions.

Referring to FIG. 7, eccentric accelerator 18, applicator roll 20 and knife roll 22 have rotated to their next respective time elapsed positions. Spindle 50 of eccentric accelerator 18 is shown in its first position along circular path 64 in its second cycle. Cutting device 80 and anvil insert 74 are also shown to have rotated with applicator roll 20 and knife roll 22 to their respective fifth rotated positions. During the counterclockwise rotation of carrier 48 between FIGS. 6 and 7, sleeve 56 of spindle 50 is rotated clockwise about axis 62, thereby causing leading end segment 30 to decelerate while allowing forward feed. Thus, the distal edge 102 of fastener material 28 extends a positive distance 'E' beyond point 104. Distance 'E' is greater than both 'A' and 'D'.

Figure 8:
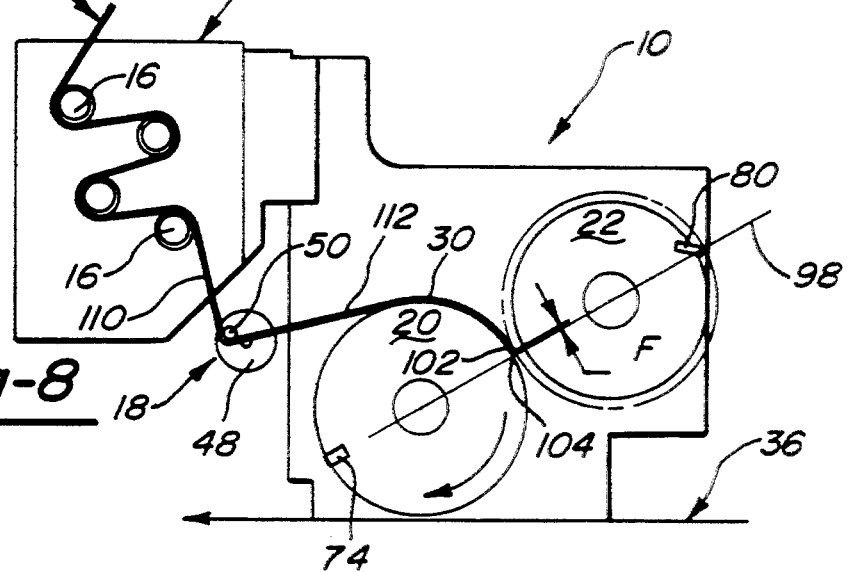
FIG. 8 is a side elevation view of the eccentric accelerator in a second rotated position of its second cycle with the anvil and knife rolls in their respective sixth rotated positions.

FIG. 8 illustrates the next respective time elapsed positions of eccentric accelerator 18, applicator roll 20 and knife roll 22. Spindle 50 of eccentric accelerator 18 is shown in its second rotated position along circular path 64 in its second cycle so as to be diametrically opposed to applicator roll 20. Simultaneously, cutting device 80 and anvil insert 74 rotate with applicator roll 20 and knife roll 22 to their respective sixth rotated positions which are diametrically opposed to point 104. During the counterclockwise rotation of carrier 48 between FIGS. 7 and 8, sleeve 56 of spindle 50 is again rotated counterclockwise about axis 62 and reverses the feeding direction of leading end segment 30. Accordingly, distal edge 102 of fastener material 28 extends a negative distance 'F' slightly behind point 104. 'F' is less than 'B' and 'C'.

Figure 9:
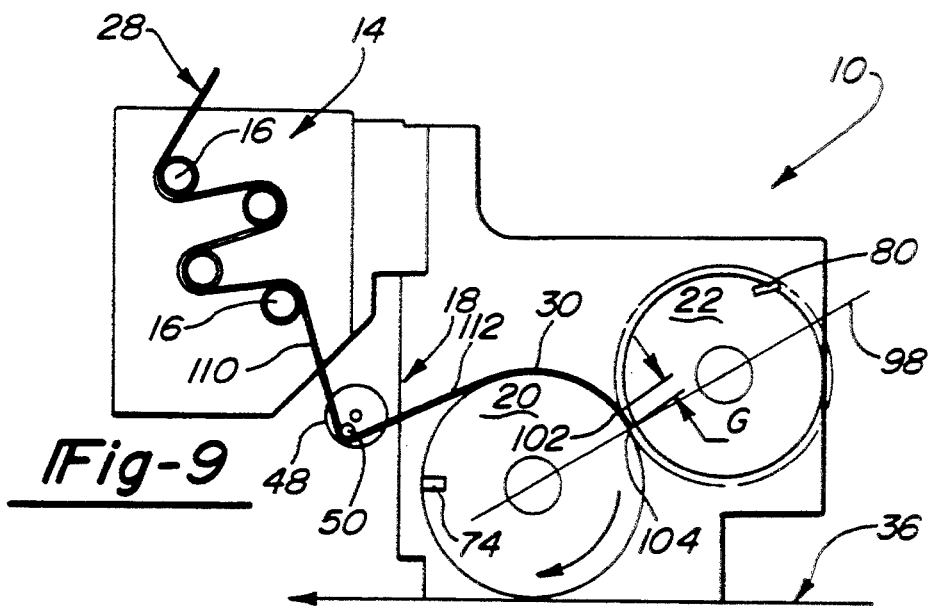
FIG. 9 is a side elevation view of the eccentric accelerator in a third rotated position of its second cycle with the anvil and knife rolls in their respective seventh rotated positions.

Eccentric accelerator 18, applicator roll 20 and knife roll 22 are then rotated to their next respective time elapsed positions, as is shown in FIG. 9. Spindle 50 of eccentric accelerator 18 is shown in its third rotated position along path 64 in its second cycle. Concurrently, cutting device 80 and anvil insert 74 rotate with applicator roll 20 and knife roll 22 to their respective seventh rotated positions. Spindle 50 again continues retraction of leading end segment 30 such that distal edge 102 of fastener material 28 is a negative distance 'G' away from point 104. 'G' is less than 'C' but greater than 'B' and 'F'.

Figure 10:
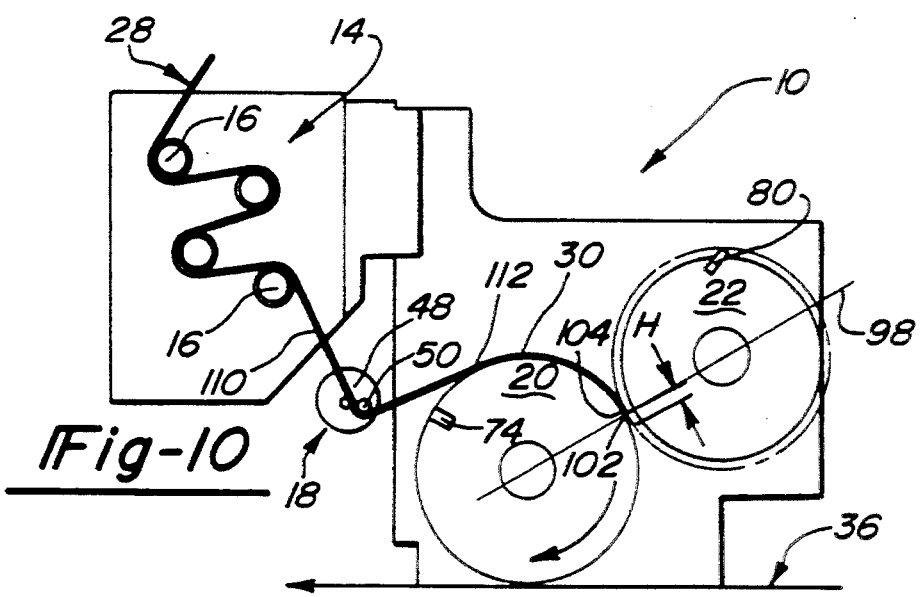
FIG. 10 is a side elevation view of the eccentric accelerator in a fourth rotated position of its second cycle with the anvil and knife rolls in their respective eighth rotated positions.

Referring now to FIG. 10, eccentric accelerator 18, applicator roll 20 and knife roll 22 have been rotated to their next respective time elapsed positions. Spindle 50 of eccentric accelerator 18 is shown in its third rotated position along path 64 which is closest to applicator roll 20. Cutting device 80 and anvil insert 74 have also been rotated with applicator roll 20 and knife roll 22 to their respective eighth rotated positions. As with the first cycle, spindle 50 is in the "matched speed" position and allows leading end segment 30 to accelerate, whereby the distal edge 102 of fastener material 28 extends a positive distance 'H' beyond point 104 which is less than 'E' and 'A' but greater than 'D'.

Figure 11:
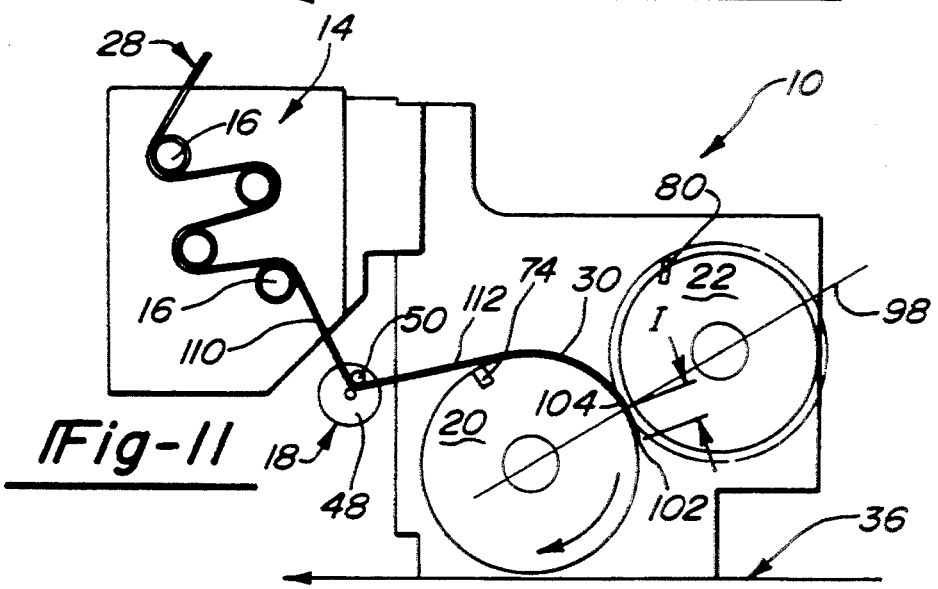
FIG. 11 is a side elevation view of the eccentric accelerator in a first rotated position of its third cycle with the anvil and knife rolls in their respective ninth rotated positions.

FIG. 11 shows eccentric accelerator 18, applicator roll 20 and knife roll 22 in their next respective time elapsed rotational positions. Spindle 50 of eccentric accelerator 18 is shown in the first position of its third cycle. Simultaneously, cutting device 80 and anvil insert 74 have rotated with applicator roll 20 and knife roll 22 to their respective ninth positions. Leading end segment 30 has again been decelerated while feeding forward. Thus, distal edge 102 of fastener material 28 extends a positive distance 'I' beyond point 104. 'I' is greater than 'H', 'E', 'D' and 'A'.

Figure 12:
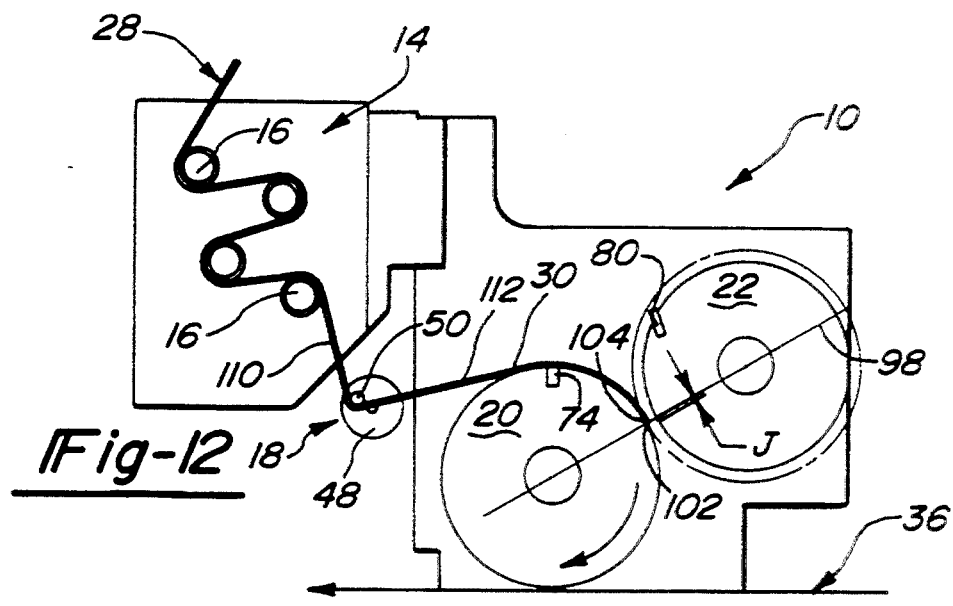
FIG. 12 is a side elevation view of the eccentric accelerator in a second rotated position of its third cycle with the anvil and knife rolls in their respective tenth rotated positions.

As seen in FIG. 12, eccentric accelerator 18, applicator roll 20 and knife roll 22 have again rotated to their respective time elapsed positions. Spindle 50 of eccentric accelerator 18 is shown in the second position of its third cycle which is diametrically opposed to applicator roll 20. Also, cutting device 80 and anvil insert 74 have rotated with applicator roll 20 and knife roll 22 to their respective tenth positions. As with the prior two eccentric accelerator 18 cycles, leading end segment 30 has been reversed such that distal edge 102 of fastener material 28 extends a positive distance 'J' beyond point 104; 'J' is less than 'I', 'H', 'E', 'D' and 'A'.

Figure 13:
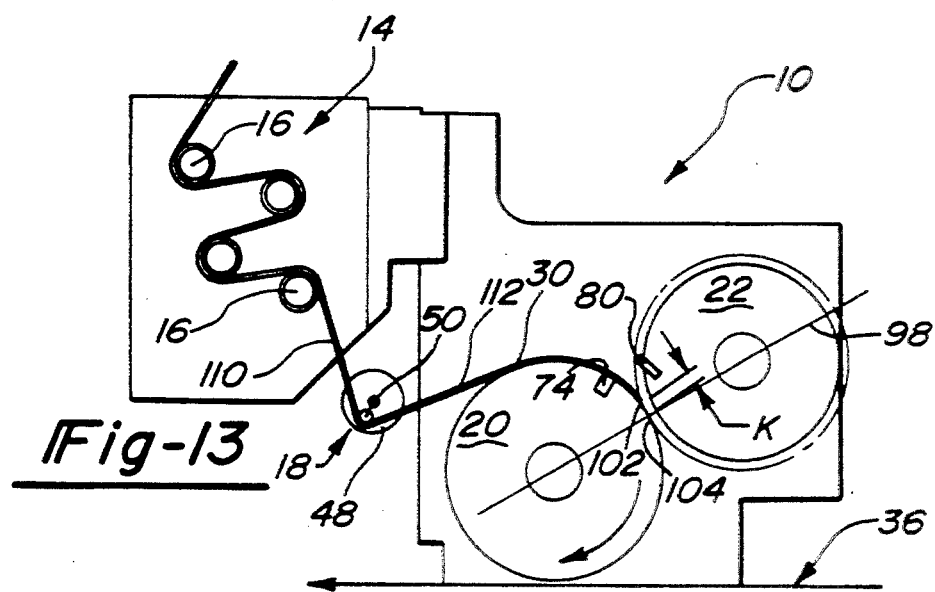
FIG. 13 is a side elevation view of the eccentric accelerator in a third rotated position of its third cycle with the anvil and knife rolls in their respective eleventh rotated positions.

FIG. 13 shows the next time elapsed positions of eccentric accelerator 18, applicator roll 20 and knife roll 22. Spindle 50 of eccentric accelerator 18 is shown in the third position of its third cycle. Simultaneously, cutting device 80 and anvil insert 74 have rotated with applicator roll 20 and knife roll 22 to their respective eleventh positions. Accordingly, distal edge 102 of fastener material 28 is a negative distance 'K' away from point 104 such that 'K' is less than 'G' but greater than 'F'.

Figure 14:
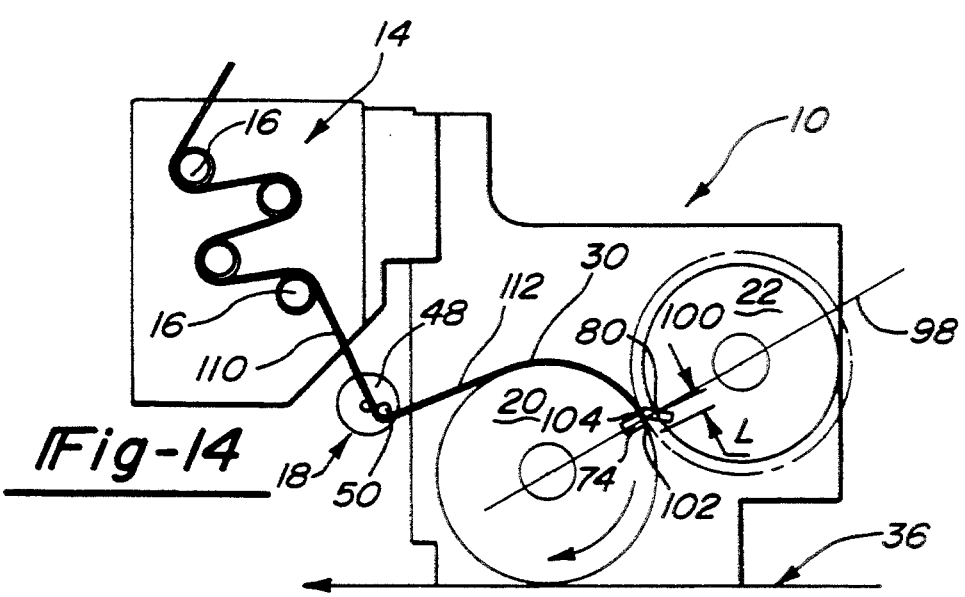
FIG. 14 is a side elevation view of the eccentric accelerator in a fourth rotated position of its third cycle with the anvil and knife rolls in their respective twelfth rotated positions, the position at which the cut occurs.

Finally, FIG. 14 shows eccentric accelerator 18, applicator roll 20 and knife roll 22 in their next respective rotational time elapsed positions. Spindle 50 of eccentric accelerator 18 is shown in the fourth position of its third cycle which is diametrically adjacent to applicator roll 20 in the "matched speed" position. Simultaneously, cutting device 80 and anvil insert 74 have rotated with applicator roll 20 and knife roll 22 to their respective twelfth positions which is coincidental with point 104. Therefore, cutting device 80 and anvil insert 74 act to cut fastener material 28 to the predetermined length 100 having a final longitudinal dimension 'L' beyond point 104.

Reference should be made again to FIG. 2. Machine 10 can be set up and operated according to the following equations when spindle 50 is in the "matched speed" position:

$$V_t = V_0 + V_1 + V_2 \tag{A}$$

$$V_t = V_0 + \underbrace{((r - 0.5d)(2\pi Q)(\cos\alpha))}_{V_1} + \underbrace{((r + 0.5d)(2\pi Q))}_{V_2}; \tag{B}$$

where "r" is a radius defined as the distance between axis 62 of spindle 50 and axis 60 of eccentric accelerator driving shaft 46 (See FIG. 1);

where "d" is defined as the diameter of eccentric roller spindle 50;

where "$\alpha$" is an angular difference between an in-feed segment 110 and an out-feed segment 112.

In-feed segment 110 is defined by the length of fastener material 28 located between the last upstream metering roll 16 and spindle 50 while out-feed segment 112 is defined by the length of fastener material 28 located between spindle 50 and applicator roll 20;

where "Q" is defined as a rotational ratio between the eccentric accelerator 18 and the applicator roll 20 (i.e., how many times eccentric accelerator 18 rotates per one revolution of applicator roll 20);

where $V_t$ is the total velocity of leading end segment 30 (See FIG. 1) of fastener material 28 when the velocity of fastener material 28 is allowed to correspond with the rotational velocity of outer circumferential surface 72 of applicator roll 20;

where $V_0$ is the constant in-feed rate or initial velocity of fastener material 28 on upstream metering roll 16 where this in-feed rate equals the amount of fastener used per diaper which equals length 'L';

where $V_1$ is the rate of change of path length of in-feed segment 110 of fastener material 28; and where $V_2$ is the rate of change of path length of out-feed segment 112 of fastener material 28.

Theoretically, angle α between in-feed segment 110 and out-feed segment 112 is ideally close to ninety degrees because this arrangement allows the spindle 50 to be at its minimum rotational velocity and thus create a minimum drag on fastener material 28 at the "matched speed" position. Furthermore, the lengths of segments 110 and 112 should be as short as possible in order to minimize the mass of fastener material 28 being manipulated and accelerated by frictional force exerted by applicator roll 20. Also, leading end segment 30 must have a sufficient length of material under the influence of the vacuum negative pressure on outer circumferential surface 72 of applicator roll 20 such that sufficient frictional force is generated to both keep the material segments 110 and 112 taut throughout the cycle and to accelerate spindle 50 during a portion of each cycle. Accordingly, this apparatus and process are capable of cyclically accelerating a slow moving web of fastener material 28 to at least twenty-eight times its feed rate at a rate of seven hundred cuts per minute.

EXAMPLE

Referring to FIGS. 1 and 2, machine 10 used to produce disposable diapers with a fastening system is preferably set up according to the parameters described hereinafter. In this example, it is intended that leading end segment 30 has a velocity equal to ninety six percent of the velocity of roll surface 72 at the time of the cut, with the velocity difference being provided to ensure that some tension is maintained for control of fastener material 28. Roll surface 72 has a velocity that substantially matches the velocity of substrate material 36. Substrate material 36 has a nominal length of 20.50 inches per diaper, but is stretched 0.625 percent at the point of application 90 of the cut segment 86 of fastener material 28. Therefore, the required total velocity $V_t$ is calculated as follows:

$V_t = (0.96)(20.50 \text{ inches/diaper})(1.00625)$
$V_t = 19.803 \text{ inches/diaper}$ Given the practical serpentine-type driving system design criterion used to construct machine 10, it has been found that the following variables accomplish the desired total velocity $V_t$:

r = 0.781 inch
α = 89°
d = 0.44 inch
Q = 3 revolutions/product
$V_0$ = 0.75 inch/diaper;

Accordingly, $V_t = 0.75 + ((0.781 - 0.22)(2)(3.1416)(3)(0.0175)) + ((0.781 + 0.22)(2)(3.1416)(3))$ therefore, $V_t = 19.803$ inches/diaper.

This equation can also be worked backwards to arrive at any of the variables. It will be understood the above example is merely intended to substantiate and set forth the novel working principles of the present invention.

While the preferred embodiment of the present invention apparatus and process for cyclically accelerating and decelerating a strip of material has been disclosed, it will be appreciated that various modifications may be made without departing from this invention. For example, such a cyclical accelerator and process can be used in forming paper products, textile products, insulated wiring products or for any other products which use multiple speed rollers. Furthermore, the described formula, preferred velocities and angles may be changed without departing from the present invention. While various materials have been disclosed in an exemplary fashion, other materials may of course also be employed. It is intended by the following claims to cover these and any other departures from the disclosed embodiments which fall within the true spirit of this invention.

What is claimed is:

1. An apparatus for use in cyclically accelerating and decelerating a leading end segment of a continuous web of material, said apparatus comprising:

first roll means having an intermediate portion of the web material wrapped thereon;

first drive means for rotatably driving said first roll means at a first rotational velocity;

second roll means having the leading end segment of the web material wrapped thereon;

second drive means for rotatably driving said second roll means at a second rotational velocity which is greater than said first rotational velocity; and an acceleration and deceleration mechanism interposed between said first and second roll means for variably changing the speed of the leading end segment while permitting said first and second roll means to be driven at their respective constant rotational velocities, said acceleration and deceleration mechanism moving in a constant direction;

said acceleration and deceleration mechanism comprising an eccentric accelerator having a carrier mounted for driven rotation about an axis and a spindle eccentrically offset from said axis, said eccentric accelerator being juxtapositioned substantially between said first roll means and said second roll means, and wherein said material is longitudinally fed around said first roll means and around a portion of said spindle of said eccentric accelerator such that the leading end segment thereof is retained on a portion of said second roll means.

2. The apparatus of claim 1 wherein said acceleration and deceleration mechanism is operable for cyclically reversing and allowing acceleration of the leading end segment relative to said second roll means for intermittently matching the speed of the leading end segment to said second rotational velocity of said second roll means.

3. The apparatus of claim 2 further comprising means for cutting a segment of the web material from the leading end segment thereof when said speed of the leading end segment equals said second rotational speed of said second roll means.

4. The apparatus of claim 3 wherein said cut segment of material is retained on said second roll means and subsequently applied thereby to a continuous web of a second material being fed through said second roll means.

5. The apparatus of claim 2 further comprising:
a vacuum generating mechanism acting in combination with said second roll means such that a negative pressure is applied to an outer circumferential surface thereof for slidably retaining the leading end segment of the web material thereon, said negative pressure generating a sufficiently low retention force such that said eccentric accelerator can variably decelerate and reverse the feeding direction of the leading end segment of the web material relative to said second rotational velocity and direction of said second roll means, said retention force simultaneously being sufficient to maintain tension in the web material and to accelerate said eccentric accelerator spindle during a portion of its rotation.

6. The apparatus of claim 3 wherein said means for cutting comprises:
an anvil insert formed in an outer circumferential surface of said second roll means; and
a cutting device being operably coordinated with said second rotational velocity of said second roll means such that the leading end segment of the web material located therebetween is cut to a predetermined longitudinal length to define said cut segment.

7. The apparatus of claim 6 further comprising:
a second web of material being continuously fed adjacent to said outer circumferential surface of said second roll means; and
third roll means located adjacent to said second roll means such that said second material is longitudinally and continuously fed therebetween;
whereby said second roll means retains and subsequently places said cut segment of the web material upon a predetermined position along said second material.

8. The apparatus of claim 7 wherein said cut segment of the first web material is retained on said outer circumferential surface of said second roll means by a negative pressure acting thereagainst.

9. The apparatus of claim 8 wherein the first material has an adhesive backing on one side thereof for adhesively bonding said cut segment to said second material.

10. The apparatus of claim 2 wherein said spindle of said eccentric accelerator further comprises:
a post extending transversely from said carrier;
a sleeve being rotationally mounted upon said post; and
bearing means being positioned between said post and said sleeve for journally supporting said sleeve for rotation relative to said post.

11. The apparatus of claim 10 wherein:
said carrier is rotatably driven in a first rotational direction;
said second roll means is rotatably driven in a second and opposite rotational direction;
said sleeve rotates in said first rotational direction when said spindle acts to decelerate and reverse the leading end segment of the material; and
said sleeve rotates in said second rotational direction when said spindle allows the leading end segment of the material to accelerate and move in the direction of rotation of said second roll means.

12. A method for accelerating and decelerating a leading end segment of a continuous web of material, said method comprising the steps of:
wrapping an intermediate segment of the web material partially around at least one upstream roll, said upstream roll being driven to feed the material in a longitudinally forward direction with a first velocity;
wrapping a leading segment of the material partially around an adjacent first portion of a downstream roll, said downstream roll having an outer circumferential surface which rotates at a substantially faster rotational velocity than does said upstream roll;
variably accelerating and decelerating the leading segment of the material by an acceleration and deceleration mechanism moving in a constant direction until the leading segment of the material has a desired velocity while said upstream and downstream rollers maintain their respective constant rotational velocities and directions.

13. The method of claim 12 further comprising:
cutting a segment of predetermined length from the leading segment of the material thereby creating a cut segment thereof;
feeding a continuous web of a second material adjacent to a second portion of said downstream roll; and
placing said cut segment of the material upon said second material at a predetermined position.

14. The method of claim 13 further comprising:
slidably retaining the leading segment of the first material partially upon said outer circumferential surface of said downstream roll by applying a negative pressure thereto;
pulling the leading segment of the first material in a direction opposite to said rotational direction of said downstream roll thereby decelerating the leading portion of said first material;
accelerating the leading segment of the first material by allowing said negative pressure along said outer circumferential surface of said downstream roller to pull said leading segment therewith; and
cyclically accelerating and decelerating the leading segment to intermittently substantially match the speed of travel of the leading end segment to the rotational velocity of said faster downstream roll immediately prior to cutting said cut segment therefrom.

15. The method of claim 14 when said cyclically accelerating and decelerating step comprises:
providing an eccentric accelerator as said acceleration and deceleration mechanism, said eccentric accelerator having a rotatable carrier mounted upon a driving shaft and a spindle eccentrically offset therefrom, said eccentric accelerator being juxtapositioned substantially between said upstream roll and said downstream roll such that the first material is longitudinally fed around said upstream roll and around a portion of said spindle of said eccentric accelerator such that the leading segment is retained on a portion of said downstream roll.

16. The method of claim 15 wherein said spindle of said eccentric accelerator further comprises:

a post extending transversely from said carrier;
a cylindrical sleeve retained on said post; and
bearings means positioned between said post and said sleeve for supporting said sleeve for rotation relative to said post.

* * * * *